(12) United States Patent
Sheldon

(10) Patent No.: US 7,942,520 B2
(45) Date of Patent: *May 17, 2011

(54) EYEWEAR WITH REFLECTIVE FRAME

(76) Inventor: Brent Sheldon, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,129

(22) Filed: Dec. 9, 2009

(65) Prior Publication Data

US 2010/0231854 A1     Sep. 16, 2010

Related U.S. Application Data

(63) Continuation-in-part of application No. 12/404,607, filed on Mar. 16, 2009, now Pat. No. 7,828,427.

(51) Int. Cl.
*G02C 11/02*     (2006.01)
(52) U.S. Cl. .............................. 351/52; 351/51; 351/121
(58) Field of Classification Search ................... 351/52, 351/51, 121, 158, 41
See application file for complete search history.

(56) References Cited

U.S. PATENT DOCUMENTS

| | | |
|---|---|---|
| 1,555,388 A | 9/1925 | Schumacher |
| D151,698 S | 11/1948 | Levoy |
| D152,487 S | 1/1949 | Mangold |
| D172,671 S | 7/1954 | Kono |
| D178,307 S | 7/1956 | Margules |
| 2,766,541 A | 10/1956 | Quinones et al. |
| D205,097 S | 6/1966 | Mitchell |
| 4,266,849 A | 5/1981 | Warner |
| 4,715,702 A | 12/1987 | Dillon |
| 4,934,792 A | 6/1990 | Tovi |
| 5,892,600 A | 4/1999 | Kuo |
| 6,020,983 A | 2/2000 | Neu et al. |
| 6,641,262 B1 | 11/2003 | Cheng |
| 6,948,808 B1 | 9/2005 | Callahan |
| 7,163,290 B2 | 1/2007 | Paolino |
| 7,261,409 B1 | 8/2007 | Taber |
| 7,364,288 B2 | 4/2008 | Huang |
| 7,828,427 B2 * | 11/2010 | Sheldon .......................... 351/52 |

FOREIGN PATENT DOCUMENTS

| | | |
|---|---|---|
| CA | 2377390 | 10/2001 |
| CA | 2504575 | 10/2005 |
| GB | 1223173 | 2/1971 |

OTHER PUBLICATIONS

Tougaw, D. et al.; "Visualizing the Future of Virtual Reality"; Computing in Science & Engineering; vol. 5, No. 4, pp. 8-11, Jul./Aug. 2003.
International Search Report dated Jun. 22, 2010, issued by the Canadian Intellectual Property Office as the PCT Searching Authority, on Applicant's related PCT International Patent Application No. PCT/CA2010/000356.
International Search Report dated Jun. 7, 2010, issued by the Canadian Intellectual Property Office as the PCT Searching Authority, on Applicant's related PCT International Patent Application No. PCT/CA2010/000357.

* cited by examiner

*Primary Examiner* — Hung X Dang
(74) *Attorney, Agent, or Firm* — Ogilvy Renault LLP

(57) ABSTRACT

Reflective eyewear include at least one lens and a substantially opaque frame having a main front section with opposed side ends for supporting the at least one lens. The frame further includes at least one retroreflective element attached to the frame to be visible by others in low-light conditions.

17 Claims, 5 Drawing Sheets

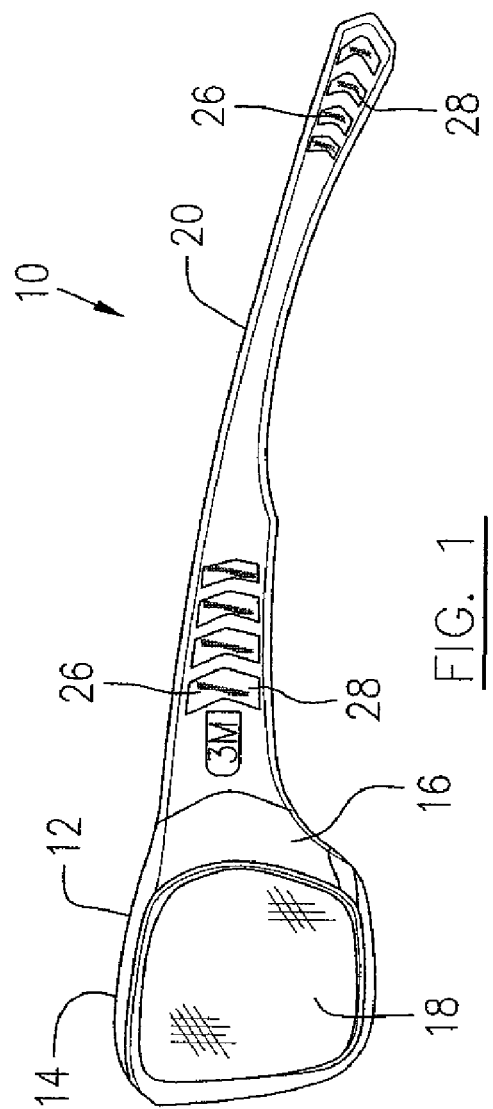
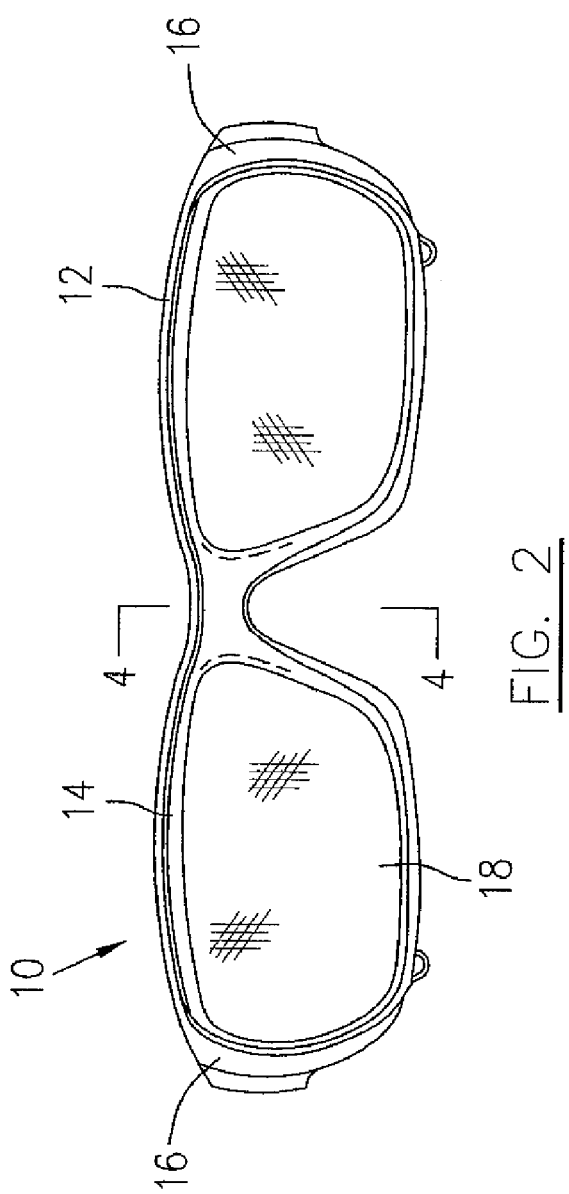
FIG. 1
FIG. 2

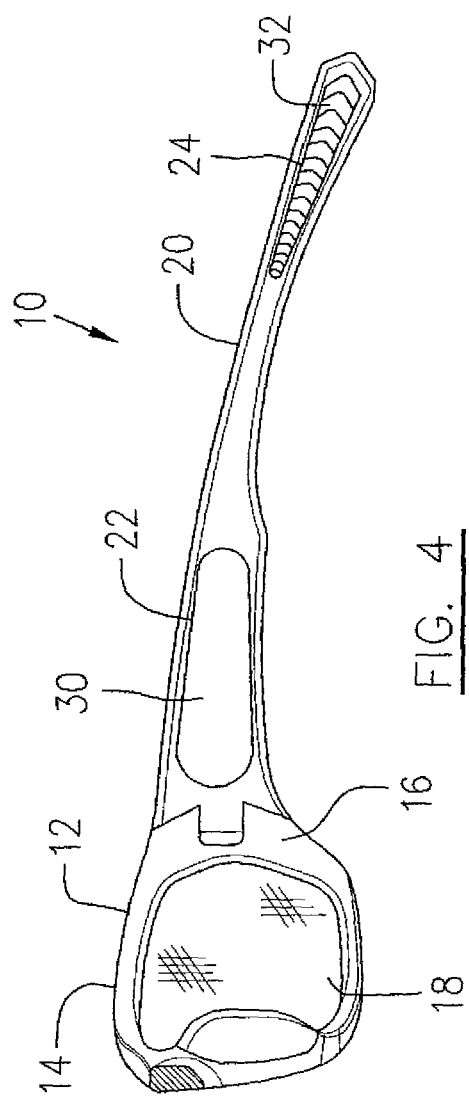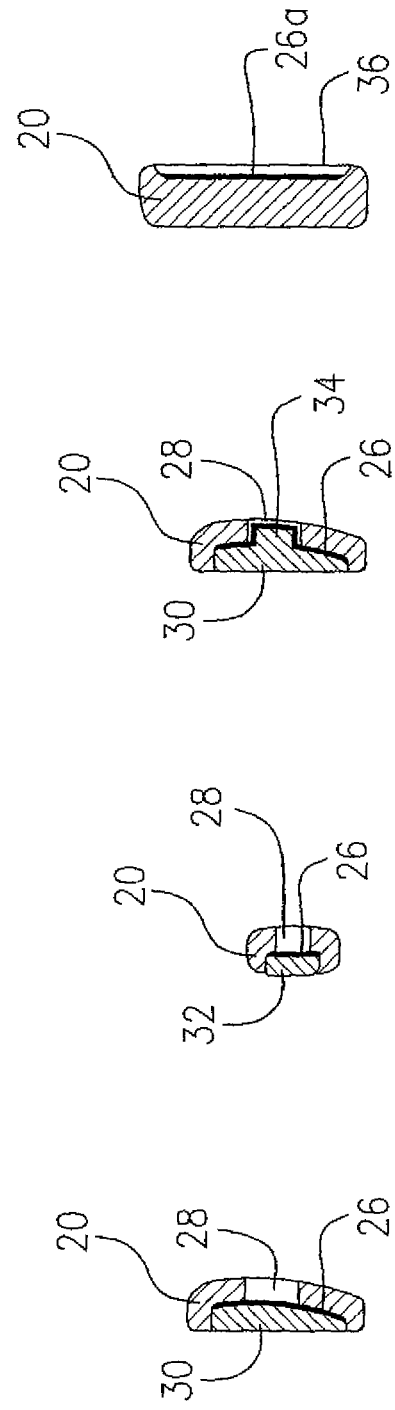

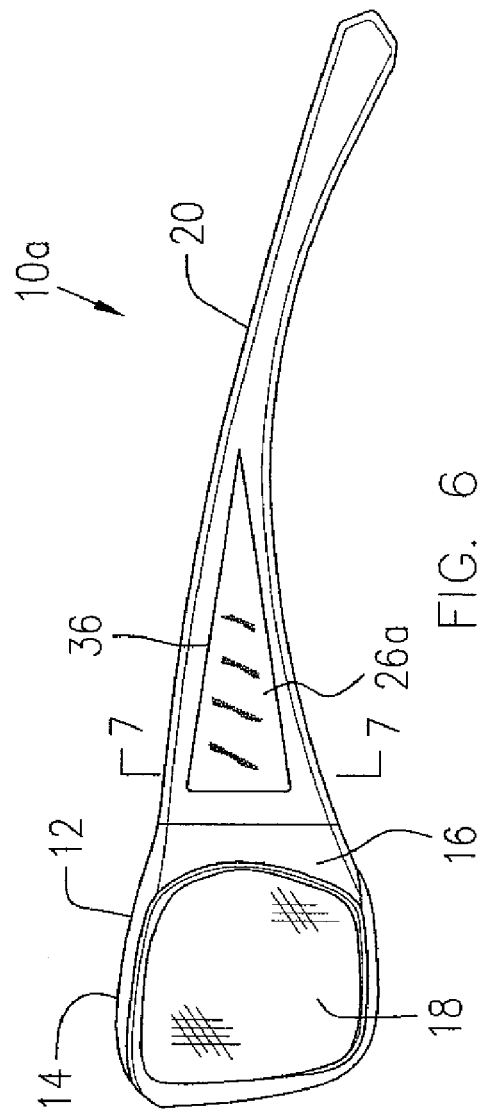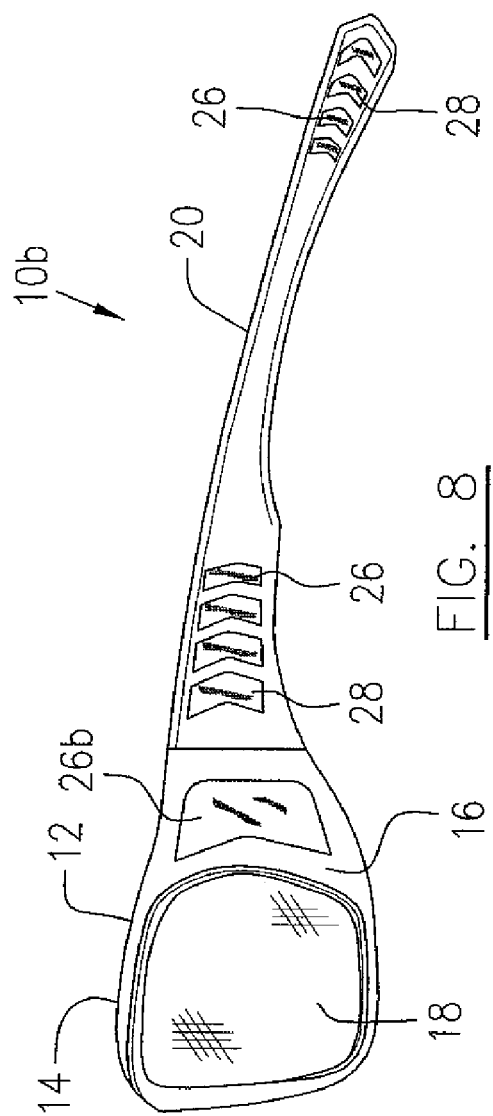

//  EYEWEAR WITH REFLECTIVE FRAME

CROSS-REFERENCE TO RELATED APPLICATIONS

This application is a Continuation-In-Part of Applicant's application Ser. No. 12/404,607, now U.S. Pat. No. 7,828,427 filed on Mar. 16, 2009.

TECHNICAL FIELD

The present invention relates to an improvement on a structure of eyewear, and more particularly to a structure of eyewear having a frame with attached retroreflective elements.

BACKGROUND OF THE INVENTION

Safety glasses are used to protect users' eyes from injuries, for example when participating in sports or while working. In some cases it is desirable to have safety glasses which are luminous or capable of reflecting light. However, such reflective safety glasses are currently not popular in the marketplace. The light-reflective feature of currently available safety glasses is not very effective due to the limited outer surface of glasses frames and the limited light reflecting capabilities of materials currently used with eyewear. It is also desirable to avoid interference with the user's vision, which may be caused by the reflection of the reflective elements of safety glasses into the user's eyes.

Accordingly, there is a need for an improved reflective eyewear including glasses and goggles.

SUMMARY OF THE INVENTION

In accordance with one aspect of the present invention, there is provided reflective eyewear comprising: at least one lens; a frame having a main front section extending between opposed side ends for supporting the at least one lens attached to the main front section, the frame further including at least one retroreflective element attached to the frame, the retroreflective element reflecting light rays of any incidence angles along a vector parallel to but opposite in direction from a light ray source.

Optionally, the frames may include side sections and the side sections may comprise a pair of arms pivotable with respect to the main front section. Also optionally, each of the side sections may comprise a base portion integrated with the main front section of the frame. Also optionally, at least one retroreflective element may be attached to the main front section, and/or each of the arms and/or the integral base portion of each side section.

Other aspects or features of the present invention will be better understood with reference to the preferred embodiments described hereinafter.

BRIEF DESCRIPTION OF THE DRAWINGS

Reference is now made to the accompanying drawings, showing by way of illustration the preferred embodiments thereof, in which:

FIG. 1 is a side elevational view of reflective safety glasses according to one embodiment, having openings in the arms to expose the retroreflective elements attached thereto;

FIG. 2 is a front elevational view of the reflective safety glasses of FIG. 1;

FIG. 4 is a cross-sectional view of the reflective safety glasses taken along line 4-4 in FIG. 2, showing an inner side of the arms with retroreflective element retaining members attached thereto;

FIG. 5A is a cross-sectional view of the arms taken along line 5A-5A of FIG. 3, showing a recess and opening defined in the arm, a retaining member and a piece of retroreflective fabric received in the recess;

FIG. 5B is a cross-sectional view of the arm taken along line 5B-5B of FIG. 3, showing a rubber holder also functioning as a retroreflective element retaining member;

FIG. 5C is a cross-sectional view of the arm similar to that of FIG. 5A, showing an alternative configuration in which a projecting element of the retaining member presses a portion of the retroreflective fabric into the opening;

FIG. 6 is a side elevational view of the reflective safety glasses according to another embodiment;

FIG. 7 is a cross-sectional view of the arm taken along line 7-7 of FIG. 6, showing a recess defined in the outer side of the arm for receiving a retroreflective element therein;

FIG. 8 is a side elevational view of reflective safety glasses according to a further embodiment.

It will be noted that throughout the appended drawings, like features are identified by like reference numerals.

DETAILED DESCRIPTION OF THE PREFERRED EMBODIMENTS

Figure 3:
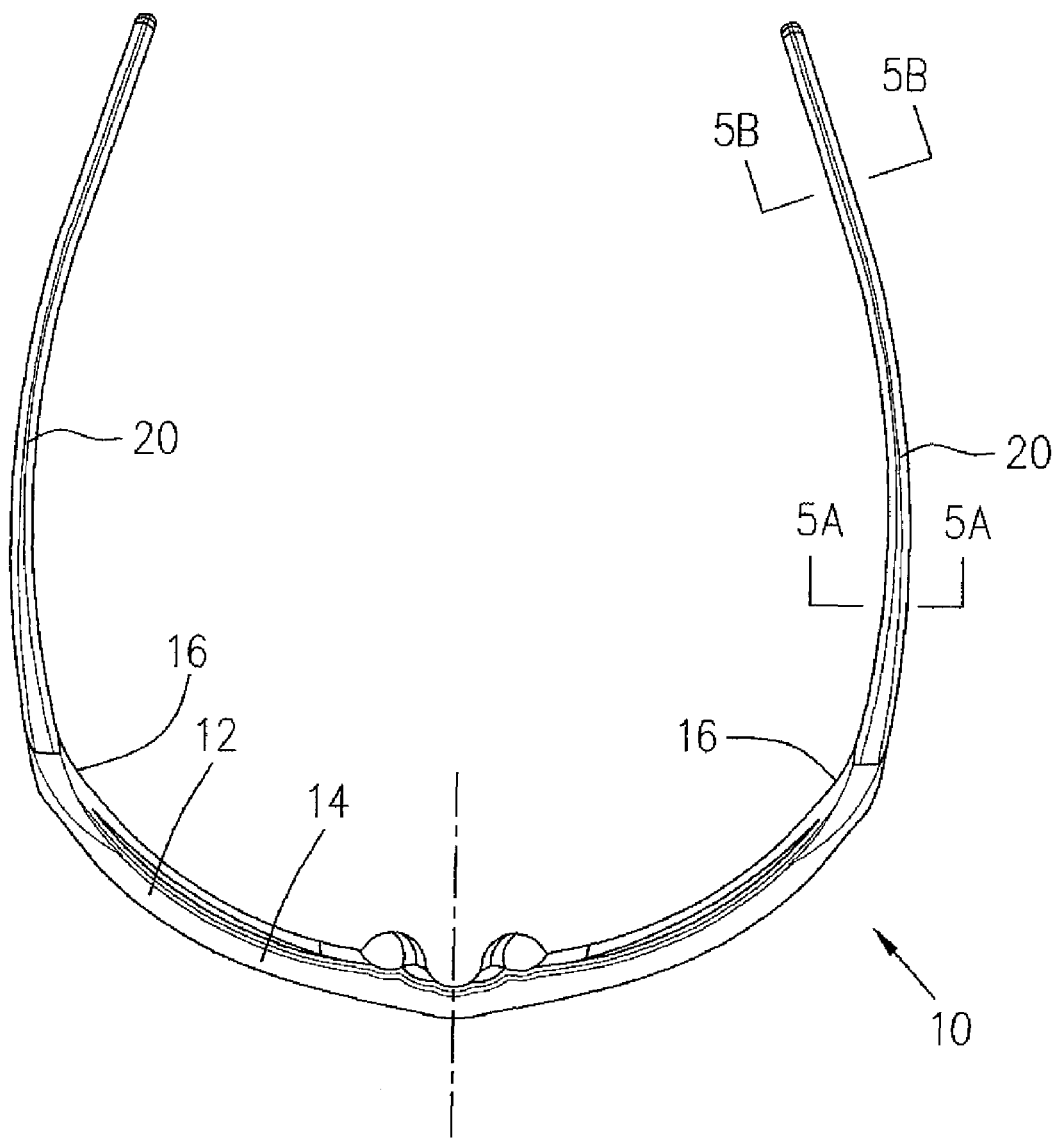
FIG. 3 is a top plan view of the reflective safety glasses of FIG. 1.

Referring to FIGS. 1 through 5B, a structure of reflective safety glasses 10 according to one embodiment generally includes a frame 12 which for example may be made of an opaque or transparent plastic material in a molding process, having a main front section 14 with opposed side ends 16 for supporting one or two lenses 18. The frame 12 further includes a pair of side sections (not numbered) extending rearwardly from the respective opposed side ends 16 of the main front section 14. The rearwardly extending side sections of the frame 14 according to this embodiment, are a pair of arms 20 pivotally joined to the respective opposed side ends 16 of the main front section 14 in a conventional manner. One or more retroreflective elements are attached to each of the side sections which are the respective arms 20 in this embodiment, such that the attached retroreflective elements are visible by others in low-light conditions.

Retroreflective materials, such as 3M™ Scotchlight™ reflective material products, use a technology to provide retroreflection which enables the human eye to perceive light in low-light conditions. In more scientific terms, retroreflection occurs when light rays are returned in the direction from which they came. An electromagnetic wave front is reflected back by a reflection surface, along a vector that is parallel to but opposite in direction from the wave source. The retroreflection surface's angle of incidence is greater than zero or equal to zero. This is unlike other conventional reflective surfaces such as a planar mirror, which does so only if the mirror is exactly perpendicular to the wave front (a zero angle of incidence). Retroreflective materials return a relatively large amount of reflected light directly to the original light source, such as a car's headlights. Since very little light is scattered when the light is returned, retroreflective materials appear brightest to an observer located near the original light source regardless of the observation angles. Therefore, retroreflective materials have been widely used for road signs and on garments but have not been used with small objects like eyewear.

In particular, the arms 20 of reflective safety glasses 10 each have a large recess 22 and a small recess 24 defined in an inner side (not numbered) of the arm 20. The large recess 22 is located near the jointed end and the small recess 24 is located near the free end of the arm 20. A piece of retroreflective fabric 26 which has reflective lenses bonded to a fabric backing to form a retroreflective surface, is placed within the respective recess 22, 24 with the retroreflective surface against a recess bottom (not numbered). Each of the recesses 22, 24 defines at least one profiled opening (a plurality of profiled openings 28 in a desired design according to this embodiment), which extends from the recess bottom through the arm 20 to an outer side (not numbered) of the arm 20 to expose the retroreflective surface of the respective retroreflective fabric 26 in a desired design.

Retaining members 30, 32 are provided within the respective recesses 22, 24 for retaining the retroreflective fabric 26 in place. Each of the retaining members 30, 32 is formed, for example with a base section (not numbered) having first and second opposed sides (not numbered). The first side of the base section substantially corresponds with the contour of the recess bottom of the respective recesses 22, 24 to press the retroreflective fabric 26 against the recess bottom. The second side of the base section of the retaining member 30 may be substantially flush with the inner side of the arm 20. The retaining member 32 may be held in position by friction or by adhesive. The retaining member 32 may be made of a soft material such as rubber to also function as a holding element of the arm 20 to hold the reflective safety glasses 10 in place on the user's head. Therefore, the second side of the base section of the retaining member 32 may be made as a slight projection on the inner side of the arm 20 for a firm contact with a user's head.

In an alternative structure as shown in FIG. 5C, the retaining member 30 may further include a projecting element 34 extending outwardly from the first side of the base section for pressing a portion of the piece of retroreflective fabric 26 into the opening 28 towards the outer side of the arm 20. The number and profile of the projecting elements 34 of the retaining member 30 will correspond with the desired design of the openings 28.

FIGS. 6 and 7 illustrate a structure of reflective safety glasses 10a according to another embodiment. Reflective safety glasses 10a include components and features indicated by numerals similar to those of reflective safety glasses 10 shown in FIGS. 1-4, and will not be redundantly described herein. The difference between the reflective safety glasses 10a and reflective safety glasses 10 of FIGS. 1-4 substantially lies in the attachment of retroreflective elements thereto. Instead of having recess 22, 24 defined in the inner side of the respective arms 20 of reflective safety glasses 10 as shown in FIG. 4, the reflective safety glasses 10a have a profiled shallow recess 36 defined in the outer side of each arm 20. A retroreflective element 26a such as a piece of retroreflective fabric having a shape substantially similar to the profile of the shallow recess 36, is received within the recess 36 and is attached thereto by, for example adhesive applied between the back of the retroreflective fabric and the recess bottom. The retroreflective surface of the fabric is therefore visible from the outer side of the arms 20.

Alternatively, the piece of retroreflective fabric used as retroreflective element 26a in reflective safety glasses 10a, may be replaced by pieces of retroreflective high gloss material or retroreflective film such as pressure-sensitive adhesive film which can be conveniently attached to the recess bottom without applying additional adhesive. Transfer film may also alternatively be used as the retroreflective element 26a. Retroreflective inks may also alternatively be used as the retroreflective element 26a for direct screen printing onto the recess bottom or at any location on the outer side of the arms 20 for decorative reflective images.

The above-mentioned alternative retroreflective materials are available in the market, and may be selected from, but not limited to 3M™ Scotchlite™ reflective materials which may be used with the reflective safety glasses 10 and 10a described herein. Any other suitable retroreflective materials may also be used as retroreflective elements for the reflective safety glasses.

FIG. 8 illustrates a structure of reflective safety glasses 10b according to a further embodiment. The reflective safety glasses 10b include the components and features indicated by numerals similar to those of reflective safety glasses 10 of FIGS. 1-4 and will not be redundantly described herein. In the reflective safety glasses 10 of FIGS. 1-4, the side sections of frame 12 generally include a pair of arms 20 only, which are pivotally attached to the opposed side ends 16 of the main front section 14. In contrast, the side sections of the reflective safety glasses 10b each include a base portion 19 integrated with the main front section 14, and extending rearwardly from the respective opposed side end 16 of the main front section 14 to provide a side shield affixed to the main front section 14 for better protection for the eyes of the user. The side sections may further include the arms 20 which are pivotally joined to a rear end (not numbered) of the respective base sections 19. Alternatively, the side sections of the frame 12 may include the base sections 19 only. An elastic head strap (not shown) instead of the arms 20, may be attached to the base sections 19 for holding the reflective safety glasses 10b to the user's head in a goggles-type configuration. A retroreflective element 26b is attached to the base sections 19 using any suitable retroreflective materials with any suitable configuration of the base sections (such as recesses, recesses with openings, a flat outer side surface, etc.), similar to or different from those discussed above with reference to embodiments 10 and 10a illustrated in FIGS. 1-5C and 6-7, respectively.

Figure 9:
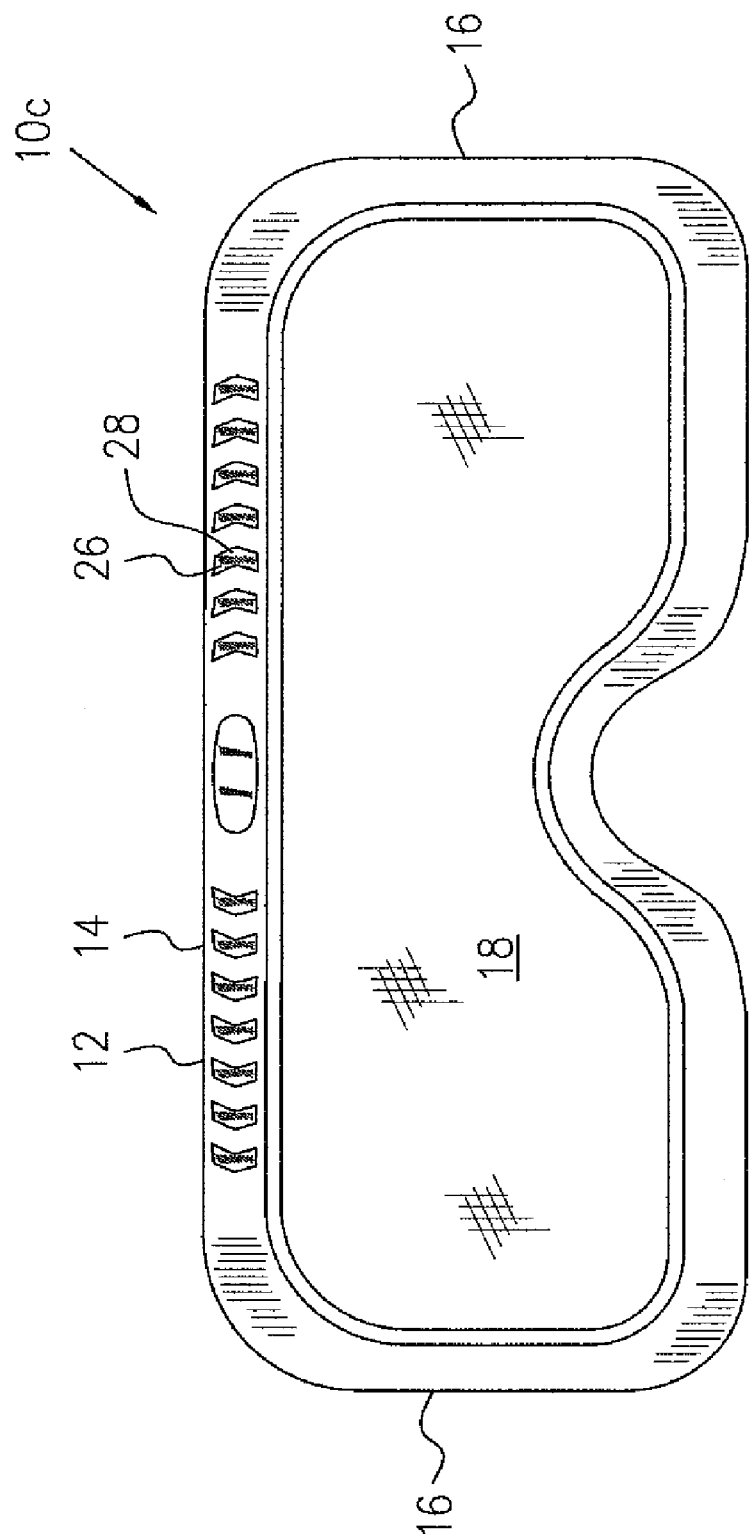
FIG. 9 is a front elevational view of reflective goggles according to a further embodiment, having the retroreflective elements attached to the main front section of the frame.

FIG. 9 illustrates reflective goggles 10c according to a further embodiment. Similar to the glasses of FIG. 2, the goggles 10c generally includes a substantially opaque or transparent frame 12 which may be made of a plastic material, having a main front section 14 with opposed side ends 16 for supporting a single lens 18. Holding device (not shown) may be provided on the back side at the respective side ends 16 of the frame 12 for attachment of a headstrap (not shown).

Retroreflective fabric 26 may be attached to the main front section 14 of the frame 12, for example, being visible through the profiled openings 28 defined in the main front section 14. The attachment of the piece of retroreflective fabric 26 to the frame 12 in this embodiment is similar to that done with glasses 10 and described with reference to FIG. 5A, 5B, 5C or similar to that shown in FIGS. 6 and 7, which will not be redundantly described herein.

The retroreflective fabric 26 may be replaced generally by other retroreflective elements, as discussed above.

According to a further embodiment, retroreflective elements such as a piece of retroreflective fabric may be added to eyewear frame structure during molding formation processes of main front sections or individual arms. Alternatively, retroreflective elements such as a transfer film may be applied on an outer surface of an eyewear frame without a recess.

The one or more retroreflective elements attached to a main front section and/or side sections of a frame of a reflective eyewear including glasses and goggles, is visible by others in low-light conditions. Those retroreflective elements attached to the eyewear can be observed from wide angles relative to the eyewear and not only from a direction restricted to a right angle relative to the reflective surface of the retroreflective elements on the eyewear provided the observer is near the light source.

The reflective safety glasses and reflective goggles of the present invention may include other components or features such as eye shields, face contact devices, etc. which are not part of this invention. Therefore, the principle of attaching retroreflective elements to a frame of eyewear as described above may be generally applicable to other types of eyewear, and is not necessarily restricted to safety glasses and goggles as described.

The embodiments of the invention described above are intended to be exemplary only. Modifications and improvements to the above-described embodiments of the present invention may become apparent to those skilled in the art in light of a review of this disclosure and are intended to fall within the scope of the appended claims.

I claim:

1. Reflective eyewear comprising:
   at least one lens;
   a frame having a main front section extending between opposed side ends for supporting the at least one lens attached to the main front section, the frame further including at least one retroreflective element attached to the frame, the retroreflective element reflecting human-eye-visible light rays of any incidence angles along a vector parallel to but opposite in direction from a human-eye-visible light ray source.

2. The eyewear as defined in claim 1 wherein the at least one retroreflective element is attached to the main front section.

3. The eyewear as defined in claim 1 wherein the frame comprises a pair of side sections extending rearwardly from the respective opposed side ends of the main front section.

4. The eyewear as defined in claim 3 wherein the at least one retroreflective element is attached to each of the side sections.

5. The structure as defined in claim 3 wherein the side sections comprise a pair of arms pivotable with respect to the main front section.

6. The eyewear as defined in claim 5 wherein the at least one retroreflective element is attached to each of the pivotable arms.

7. The eyewear as defined in claim 3 wherein each of the side sections comprises a base portion integrated with the main front section.

8. The eyewear as defined in claim 7 wherein the at least one retroreflective element is attached to the integral base portion of each side section.

9. The eyewear as defined in claim 1 wherein the at least one retroreflective element is a piece of retroreflective fabric.

10. The structure as defined in claim 1 wherein the at least one retroreflective element is a piece of retroreflective high gloss material.

11. The structure as defined in claim 1 wherein the at least one retroreflective element is a piece of retroreflective pressure-sensitive adhesive film.

12. The structure as defined in claim 1 wherein the frame comprises a recess defined in an outer side thereof for receiving the at least one retroreflective element.

13. The eyewear as defined in claim 1 wherein the frame comprises a recess defined in an inner side thereof for receiving a piece of retroreflective fabric, the recess defining an opening extending from a recess bottom through the frame to an outer side of the frame to expose a functioning surface of the piece of retroreflective fabric.

14. The eyewear as defined in claim 13 wherein the frame comprises a retaining member attached to the inner side for retaining the piece of retroreflective fabric in the recess.

15. The eyewear as defined in claim 14 wherein the retaining member comprises a base section received in the recess and having first and second opposed sides, the first side substantially contoured to correspond with the recess bottom in order to allow the retroreflective fabric to be pressed against the recess bottom.

16. The structure as defined in claim 15 wherein the second side of the retaining member is substantially flush with the inner side of the respective side sections.

17. The structure as defined in claim 15 wherein the retaining member comprises a projecting element extending outwardly from the first side of the base section for pressing a portion of the piece of retroreflective fabric into the opening towards the outer side of the frame.

* * * * *